(12) United States Patent
Xu et al.

(10) Patent No.: US 12,383,897 B2
(45) Date of Patent: Aug. 12, 2025

(54) MULTI-CHANNEL MICROFLUIDIC BLOOD COAGULATION DETECTION CHIP

(71) Applicant: LANSION BIOTECHNOLOGY CO., LTD., Jiangsu (CN)

(72) Inventors: Xingshang Xu, Jiangsu (CN); Jeffery Chen, Jiangsu (CN)

(73) Assignee: LANSION BIOTECHNOLOGY CO., LTD., Jiangsu (CN)

( * ) Notice: Subject to any disclaimer, the term of this patent is extended or adjusted under 35 U.S.C. 154(b) by 1016 days.

(21) Appl. No.: 17/435,398

(22) PCT Filed: Apr. 13, 2020

(86) PCT No.: PCT/CN2020/084387
§ 371 (c)(1),
(2) Date: Sep. 1, 2021

(87) PCT Pub. No.: WO2020/177774
PCT Pub. Date: Sep. 10, 2020

(65) Prior Publication Data
US 2022/0143600 A1    May 12, 2022

(30) Foreign Application Priority Data

Mar. 1, 2019   (CN) .......................... 201920260232.9

(51) Int. Cl.
*B01L 3/00*  (2006.01)
*G01N 33/49*  (2006.01)

(52) U.S. Cl.
CPC ..... *B01L 3/50273* (2013.01); *B01L 3/502715* (2013.01); *G01N 33/4905* (2013.01);
(Continued)

(58) Field of Classification Search
CPC ........... B01L 3/50273; B01L 3/502715; B01L 2200/0684; B01L 2300/0645; B01L 2300/0819; B01L 2300/0887
See application file for complete search history.

(56) References Cited

U.S. PATENT DOCUMENTS

| 2014/0190830 A1* | 7/2014 | Sturmer | B01L 3/50273 324/691 |
|---|---|---|---|
| 2017/0014822 A1 | 1/2017 | Ker | |
| 2018/0074039 A1* | 3/2018 | Soper | B01L 3/502761 |

FOREIGN PATENT DOCUMENTS

| CN | 2559986 | 7/2003 |
|---|---|---|
| CN | 107118938 | 9/2017 |

(Continued)

OTHER PUBLICATIONS

"International Search Report (Form PCT/ISA/210)" of PCT/CN2020/084387, with English translation thereof, mailed on Jul. 9, 2020, pp. 1-6.

(Continued)

*Primary Examiner* — Jill A Warden
*Assistant Examiner* — Dwayne K Handy
(74) *Attorney, Agent, or Firm* — JCIP GLOBAL INC.

(57) ABSTRACT

A multi-channel microfluidic blood coagulation detection chip includes a chip body. The chip body includes a lower-layer chip, a middle-layer chip, and an upper-layer chip in sequence from bottom to top. The lower-layer chip, the middle-layer chip, and the upper-layer chip cooperate with each other to define a closed microfluidic channel and a plurality of mutually-independent detection chambers. The upper-layer chip is provided with a sample loading hole, and the sample loading hole communicates with the detection chambers through the microfluidic channel. The chip body further includes electrodes. The electrodes include upper-layer electrodes and lower-layer electrodes, the upper-layer
(Continued)

electrodes are disposed on a back surface of the upper-layer chip, the lower-layer electrodes are disposed on a front surface of the lower-layer chip, and a gap is provided between the upper-layer electrodes and the lower-layer electrodes.

13 Claims, 4 Drawing Sheets

(52) U.S. Cl.
CPC ............. *B01L 2200/0684* (2013.01); *B01L 2300/0645* (2013.01); *B01L 2300/0819* (2013.01); *B01L 2300/0887* (2013.01)

(56) References Cited

FOREIGN PATENT DOCUMENTS

| | | |
|---|---|---|
| CN | 107855142 | 3/2018 |
| CN | 108398470 | 8/2018 |
| CN | 108535464 | 9/2018 |
| CN | 108745429 | 11/2018 |
| CN | 209829010 | 12/2019 |
| EP | 0978722 | 2/2000 |

OTHER PUBLICATIONS

"Written Opinion of The International Searching Authority (Form PCT/ISA/237)" of PCT/CN2020/084387, mailed on Jul. 9, 2020, pp. 1-5.

\* cited by examiner

MULTI-CHANNEL MICROFLUIDIC BLOOD COAGULATION DETECTION CHIP

CROSS-REFERENCE TO RELATED APPLICATION

This application is a 371 of international application of PCT application serial no. PCT/CN2020/084387, filed on Apr. 13, 2020 which claims the priority benefit of China application no. 201920260232.9, filed on Mar. 1, 2019. The entirety of each of the above mentioned patent applications is hereby incorporated by reference herein and made a part of this specification.

BACKGROUND

Technical Field

The present disclosure relates to the technical field of medical devices, and in particular, to a multi-channel microfluidic blood coagulation detection chip.

Description of Related Art

Microfluidics is a technology applied across various disciplines including engineering, physics, chemistry, microtechnology, and biotechnology. Microfluidics involves the study of micro-fluids and the study of how to manipulate, control and use such small volumes of fluids in various microfluidic systems and devices such as microfluidic chips. For example, microfluidic biochips (referred to as "lab-on-a-chip") are used in the field of molecular biology to integrate assay operations for purposes such as analyzing enzymes and DNA, detecting biochemical toxins and pathogens, and diagnosing diseases.

Microfluidic chip relates to a hot field in the current development of miniaturized total analysis systems. Microfluidic chip analysis takes a chip as an operating platform, analytical chemistry as the basis, a micro-electromechanical processing technology as the support, a micro-pipeline network as a structural feature, and life sciences as the main application object at present, and is the focus of the current development in the field of miniaturized total analysis systems. The goal of the microfluidic chip analysis is to integrate the functions of the entire laboratory, including sampling, dilution, reagent addition, reaction, separation, and detection, on a microchip. Microfluidic chip is the main platform for the realization of microfluidic technologies. Main device features of the microfluidic chip are that the effective structures (channels, detection chambers and some other functional components) containing fluids are micron-scale-sized in at least one dimension. Due to the micron-scale structure, the fluid exhibits and produces special properties therein that are different from those at the macro scale. Therefore, unique analysis-generated properties have been developed. Features and development advantages of the microfluidic chip are as follows. The microfluidic chip is characterized by controllable liquid flow, minimal consumption of samples and reagents, and an increase in analysis speed by ten times or hundreds of times, and simultaneous analysis of hundreds of samples can be performed in a few minutes or even less, and the entire process of sample pretreatment and analysis can be realized online. The application purpose of the microfluidic chip is to achieve the ultimate goal of the miniaturized total analysis systems, i.e., the lab-on-a-chip, and the key application field of current work development is the field of life sciences.

Current international research status is as follows. Innovations are mostly focused on separation and detection systems, and the research on a number of issues about how to introduce actual samples for analysis on the chip, such as sample introduction, sample change, and pretreatment, is still very weak. The development depends on interdisciplinary development.

Chinese patent publication of CN108398470A discloses a biosensor for blood activated clotting time determination, including a bottom layer, a middle layer, and an upper layer stacked and connected in sequence. The upper layer is provided with a sample loading channel and a ventilation channel, and both the sample loading channel and the ventilation channel run through the upper layer in the thickness direction. The middle layer is provided with at least one sample deposition hole, at least one diffusion channel, and at least one detection cell. The detection cell communicates with the sample deposition hole through the diffusion channel, and the detection cell runs through the middle layer in the thickness direction. The upper surface of the bottom layer is provided with a working electrode and a reference electrode; the sample loading channel is located above the sample deposition hole and communicates with the sample deposition hole. The ventilation channel is located above the detection cell and communicates with the detection cell. The surface regions of the bottom layer and the upper layer facing and corresponding to the detection cell cooperate with the cell wall of the detection cell to enclose a sample detection cavity. One ends of both the working electrode and the reference electrode are located in the sample detection cavity, and the other ends extend beyond the middle layer and the upper layer to form connection ends to connect to a detection instrument. Both an upper cavity wall of the sample detection cavity and a lower cavity wall between the working electrode and the reference electrode are provided with a dry clotting promoter coating. In the biosensor for blood activated clotting time determination, although multiple channels and multiple detection chambers are designed for simultaneous detection, the multiple detection chambers use the same reference electrode, and the reference electrode and the working electrode are both designed on the bottom layer. The interference between the electrodes in such a design is great, which may affect the accuracy of sample detection results in an actual detection process.

Chinese patent document (application no. 201810599700.5) discloses a microfluidic detection chip for multi-channel rapid detection, including a chip body. A chip sampling port, a plurality of mutually-independent detection chambers, and a microfluidic channel are disposed on the chip body, and the chip sampling port communicates with the detection chambers through the microfluidic channel. The chip body further includes electrodes; the detection chambers are connected to the electrodes. The microfluidic channel includes a main flow channel and a plurality of branching microfluidic channels. The tail end of the main flow channel is divided into the plurality of branching microfluidic channels, and the plurality of branching microfluidic channels communicate in one-to-one correspondence with the plurality of mutually-independent detection chambers. The other end of the main flow channel communicates with the chip sampling port. The microfluidic detection chip for multi-channel rapid detection is a three-layer chip, and the size of the chip body is about 8~10 cm*2.4~2.8 cm, and therefore, the size of the chip is too large.

Therefore, it is necessary to develop a multi-channel microfluidic blood coagulation detection chip which decreases the mutual interference between electrodes by reasonably designing the electrodes, and has large detection throughput, high detection efficiency and accuracy, as well as smaller volume and lower cost.

SUMMARY

The technical problem to be solved by the present disclosure is to provide a multi-channel microfluidic blood coagulation detection chip which decreases the mutual interference between electrodes by reasonably designing the electrodes, and has large detection throughput, high detection efficiency and accuracy, as well as smaller volume and lower cost.

In order to solve the above-mentioned technical problem, the technical solution adopted in the present disclosure is that, the multi-channel microfluidic blood coagulation detection chip includes a chip body. The chip body includes, in sequence from bottom to top, a lower-layer chip, a middle-layer chip, and an upper-layer chip. The lower-layer chip, the middle-layer chip, and the upper-layer chip cooperate with each other to define a closed microfluidic channel and a plurality of mutually-independent detection chambers. The upper-layer chip is provided with a sample loading hole, and the sample loading hole communicates with the detection chambers through the microfluidic channel. The chip body further includes electrodes. The electrodes include upper-layer electrodes and lower-layer electrodes, the upper-layer electrodes are disposed on the back surface of the upper-layer chip, the lower-layer electrodes are disposed on the front surface of the lower-layer chip, and a gap is provided between the upper-layer electrodes and the lower-layer electrodes.

By using the above-mentioned technical solution, microfluidic chip detection has the characteristics of high accuracy, fast speed and low detection cost, and is suitable for detection in precision medical links. By designing the upper-layer electrodes and the lower-layer electrodes, the electrodes of the multi-channel microfluidic blood coagulation detection chip are arranged in two layers, so that the mutual interference between the electrodes can be reduced, thereby improving the accuracy of detection results. The chip using a three-layer structure including the lower-layer chip, the middle-layer chip and the upper-layer chip is reasonable in design and simple and compact in structure. Moreover, the size of the multi-channel microfluidic blood coagulation detection chip can also be decreased, so that the chip body is smaller and more portable, and the production cost is lowered. Detection reagents are pre-embedded in the detection chambers, so that multiple coagulation indexes can be detected simultaneously. The chip is simple in structure and easy to operate, improves the detection efficiency, and greatly reduces the consumption of resources. Thus, quick detection is realized, and the cost is lowered.

The further improvement of the present disclosure is that, both the upper-layer electrodes on the back surface of the upper-layer chip and the lower-layer electrodes on the front surface of the lower-layer chip are arranged corresponding to positions where the detection chambers of the middle-layer chip are located, and the upper-layer electrodes and the lower-layer electrodes communicate with each other through the detection chambers. The detection reagents are pre-embedded in the detection chambers, and after blood to be tested flows into the detection chambers, both the upper-layer electrodes and the lower-layer electrodes are in contact with the blood in the detection chambers, thereby realizing electrically conductive communication through the blood.

The further improvement of the present disclosure is that, the middle-layer chip is provided with middle-layer communication holes at positions corresponding to the upper-layer electrodes, the lower-layer chip is provided with lower-layer communication holes at positions corresponding to the upper-layer electrodes, and the upper-layer electrodes are in contact and connection with a detection instrument through the middle-layer communication holes and the lower-layer communication holes. Such a setting enables the upper-layer electrodes on the back surface of the upper-layer chip to be in direct contact and connection with the detection instrument.

The further improvement of the present disclosure is that, both the microfluidic channel and the detection chambers run through the middle-layer chip; the microfluidic channel includes a main flow channel and a plurality of branching microfluidic channels, the tail end of the main flow channel is divided into the plurality of branching microfluidic channels, and the plurality of branching microfluidic channels communicate in one-to-one correspondence with the plurality of mutually-independent detection chambers; and the front end of the main flow channel communicates with the sample loading hole. Designing the main flow channel and the plurality of branching microfluidic channels in a specific structural form to guide the flow of a blood sample allows for simultaneous injection of the sample from one sample chamber into a plurality of reaction chambers without contaminating the sample, thereby facilitating sample injection. After the sample is injected from the sample loading hole, the sample flows from the main flow channel to the plurality of branching microfluidic channels simultaneously, and then enters the plurality of mutually-independent detection chambers. The detection reagents are pre-embedded in the detection chambers, so that multiple coagulation indexes can be detected simultaneously, and a multi-channel effect is achieved. The chip is simple in structure and easy to operate, improves the detection efficiency, and greatly reduces the consumption of resources. Thus, quick detection is realized, and the cost is lowered.

The further improvement of the present disclosure is that, the upper-layer electrodes include a plurality of first electrodes, and the plurality of first electrodes are all arranged in one-to-one correspondence with the plurality of mutually-independent detection chambers; the lower-layer electrodes include a plurality of second electrodes, the plurality of second electrodes are all arranged in one-to-one correspondence with the plurality of mutually-independent detection chambers, and the first electrodes and the second electrodes are respectively working electrodes or reference electrodes. A first electrode and a second electrode are correspondingly provided for each detection chamber, respectively, so as to separate the electrodes of each detection chamber, thereby reducing the interference between the electrodes, and improving the detection accuracy.

The further improvement of the present disclosure is that, one ends of the plurality of first electrodes are arranged in one-to-one correspondence with the plurality of mutually-independent detection chambers and located in the detection chambers, and the other ends of the plurality of first electrodes extend on the back surface of the upper-layer chip to the end head of one end of the upper-layer chip to form connection ends in contact and connection with the detection instrument. Such a setting enables the first electrode corresponding to each detection chamber to be in contact and connection with the detection instrument through the connection end, thereby reducing interference with the second electrode.

The further improvement of the present disclosure is that, one ends of the plurality of second electrodes are arranged in one-to-one correspondence with the plurality of mutually-independent detection chambers and located in the detection chambers, and the other ends of the plurality of second electrodes extend on the front surface of the lower-layer chip to the end head of one end of the lower-layer chip to form detection ends in connection with the detection instrument, and the detection ends are exposed outside the end of an integral whole, formed by bonding the lower-layer chip, the middle-layer chip and the upper-layer chip, with respect to the upper-layer chip and the middle-layer chip. Such a setting enables the detection ends of the lower-layer chip to be directly inserted into the detection instrument, thereby avoiding interference with the upper-layer electrodes.

The further improvement of the present disclosure is that, the upper-layer chip is further provided with a plurality of vent holes, and the plurality of vent holes are all arranged in one end of the upper-layer chip and disposed at positions corresponding to the detection chambers. By providing the plurality of vent holes that run through the upper-layer chip, the flow resistance of the fluid to be tested is reduced, so that the flow is faster, and the detection chambers can be quickly filled. The setting of the vent holes facilitates the flow of the sample and is convenient for sample injection. If there is no vent hole, the sample cannot flow into the detection chambers for reaction, and the detection reagents are pre-embedded in the detection chambers.

The further improvement of the present disclosure is that, the connection ends are arranged in one-to-one correspondence with the middle-layer communication holes and the lower-layer communication holes, respectively. One middle-layer communication hole corresponds to one lower-layer communication hole and to one connection end. In this way, each first electrode can be in contact with the detection instrument.

As a preferred technical solution of the present disclosure, the middle-layer chip is provided with a liquid receiving port, the liquid receiving port is disposed corresponding to the position of the sample loading hole, one end of the main flow channel is connected to the liquid receiving port, the other end of the main flow channel is connected to the detection chambers through the branching microfluidic channels, and the width of the detection chambers is greater than the width of the branching microfluidic channels. The sample loading hole using this structure is easy for sample injection, avoids contamination, and is simple in structure and low in cost.

As a preferred technical solution of the present disclosure, the main flow channel extends in a horizontal direction to the end away from the liquid receiving port to be provided with a first branching microfluidic channel that is connected to a first detection chamber; the main flow channel extends in a vertical direction to the end away from the liquid receiving port towards both sides respectively to be provided with a second branching microfluidic channel and a third branching microfluidic channel; the second branching microfluidic channel extends in a direction parallel to the main flow channel to both ends respectively to connect to a second detection chamber and a third detection chamber, and the third branching microfluidic channel extends in the direction parallel to the main flow channel to both ends respectively to connect to a fourth detection chamber and a fifth detection chamber. Designing the main flow channel and the plurality of branching microfluidic channels in a specific structural form to guide the flow of a blood sample allows for simultaneous injection of the sample from one sample chamber into a plurality of reaction chambers, which makes the flow faster and improves the detection efficiency. In addition, such a design decreases the size of the multi-channel microfluidic blood coagulation detection chip. Compared with the multi-channel microfluidic blood coagulation detection chip of a three-layer structure previously claimed by the applicant, the length and width are decreased by 25%-45%, therefore, the production cost is lowered, and the chip is smaller and more portable. Furthermore, five detection chambers are provided, allowing for simultaneous detection of five coagulation indexes of the blood sample.

As a preferred technical solution of the present disclosure, the number of both the first electrodes and the second electrodes is five, and correspondingly, the number of both the middle-layer communication holes and the lower-layer communication holes is five. The number of both the corresponding connection ends and detection ends is also five.

As a preferred technical solution of the present disclosure, each of the connection ends is a rectangle of the same size, and the spacing between each two of the connection ends is equal; correspondingly, each of the middle-layer communication holes and each of the lower-layer communication holes are both rectangles of the same size, and the spacing between each two of the middle-layer communication holes and the spacing between each two of the lower-layer communication holes are both equal; the size of the connection ends is greater than or equal to the size of the middle-layer communication holes and the lower-layer communication holes; and the middle-layer communication holes have the same size as the lower-layer communication holes.

As a preferred technical solution of the present disclosure, the shape of each of the detection ends is rectangular and the spacing between each two of the detection ends is equal; and the length of the detection ends exposed outside the end of the integral whole that is formed by bonding the lower-layer chip, the middle-layer chip and the upper-layer chip, with respect to the upper-layer chip and the middle-layer chip is not more than 1 cm. The rectangle of the detection end at the farthest position that abuts against an end of the lower layer chip is the widest. This setting is mainly because this detection end needs to cooperate with the detection instrument to prompt whether the chip electrodes communicate with the instrument. The rectangles of the remaining detection ends are the same in size.

As a preferred technical solution of the present disclosure, the plurality of the vent holes are all disposed in the end portions of the detection chambers away from the branching microfluidic channels and at corresponding positions flush with the edges of the detection chambers.

The further improvement of the present disclosure is that, the lower-layer chip, the middle-layer chip, and the upper-layer chip are bonded into an integral whole by double-sided gluing of the middle-layer chip.

As a preferred technical solution of the present disclosure, the middle-layer chip is a double-sided adhesive tape, the material for the upper-layer chip and/or the lower-layer chip is any one of PMMA, PP, PE, and PET, and the surfaces of the upper-layer chip and the lower-layer chip each are provided with a hydrophilic membrane, so that the sample quickly flows into the main flow channel through the sample loading hole, and then separately flows to each branching microfluidic channel. The middle-layer chip is preferably a pressure-sensitive adhesive tape. With this technical solution, materials are easily available, and the manufacturing process of the pressure-sensitive adhesive tape allows for accurate control of the thickness thereof. Therefore, with this technical solution, the depth and size of the microfluidic channel can be accurately controlled, and the depth control of the detection chambers is also facilitated, so that the thickness deviation of each detection chamber of the microfluidic chip is small, the consistency is high, and the detection accuracy is improved. The surfaces of the upper-layer chip and the lower-layer chip each are provided with a hydrophilic membrane, so that the sample quickly flows into the main flow channel through the sample loading hole, and then separately flows to each branching microfluidic channel. In this way, the flow speed is accelerated, and the detection efficiency can be improved.

As a preferred technical solution of the present disclosure, the thickness of the middle-layer chip is 0.1~1.0 mm; and the surface of the lower-layer chip is level, the depth of the closed microfluidic channel defined by the lower-layer chip, the middle-layer chip, and the upper-layer chip in cooperation is 0.1~1.0 mm, and the widths of the detection chambers defined by the three layers of chips in cooperation are 1.0~2.0 mm.

As a preferred technical solution of the present disclosure, each of the branching microfluidic channels is provided with a nozzle at a junction with the detection chamber, and the thickness of the electrodes is 0.5 mm. Nozzles are provided at the junctions between the branching microfluidic channels and the detection chambers to enable the sample to flow into the detection chamber more easily and quickly. The function of the electrodes is to receive signals generated by blood reaction in the detection chambers while applying an alternating-current voltage. The detection ends and the connection ends are inserted into the detection instrument to monitor electrochemical signals generated by reaction, and work in conjunction with the supporting detection instrument to obtain detection results. The detection ends of the lower-layer electrodes are the portions of the integral whole, formed by bonding the lower-layer chip, the middle-layer chip and the upper-layer chip, that are exposed with respect to the upper-layer chip and the middle-layer chip, so that the detection ends of the lower-layer chip can be inserted into the detection instrument more easily and conveniently.

Compared with the prior art, according to the multi-channel microfluidic blood coagulation detection chip, arranging the upper-layer electrodes and the lower-layer electrodes in two layers reduces the mutual interference between the electrodes and improves the accuracy of the detection results. In addition, designing the main flow channel and the plurality of branching microfluidic channels in a specific structural form to guide the flow of a blood sample allows for simultaneous injection of the sample from one sample chamber into a plurality of reaction chambers without contaminating the sample, thereby facilitating sample injection, and decreasing the size of the multi-channel microfluidic blood coagulation detection chip. Compared with the multi-channel microfluidic blood coagulation detection chip of a three-layer structure previously claimed by the applicant, the length and width are decreased by 25%-45% (the length and width of the chip claimed previously are 8~10 cm*2.4~2.8 cm, and the length and width of this multi-channel microfluidic blood coagulation detection chip are 5~7 cm*1.6~2.0 cm), therefore, the production cost is lowered, and the chip is smaller and more portable. After the sample is injected from the sample loading hole, the sample flows from the main flow channel to the plurality of branching microfluidic channels simultaneously, and then enters the plurality of mutually-independent detection chambers. In this way, multiple coagulation indexes can be detected simultaneously, and the multi-channel effect is achieved. The chip is simple in structure and easy to operate, improves the detection efficiency and accuracy, and greatly reduces the consumption of resources. Thus, quick detection is realized, and the cost is lowered.

BRIEF DESCRIPTION OF THE DRAWINGS

The detailed description is further provided below with reference to the accompanying drawings and embodiments of the present disclosure.

DESCRIPTION OF THE EMBODIMENTS

Figure 1:
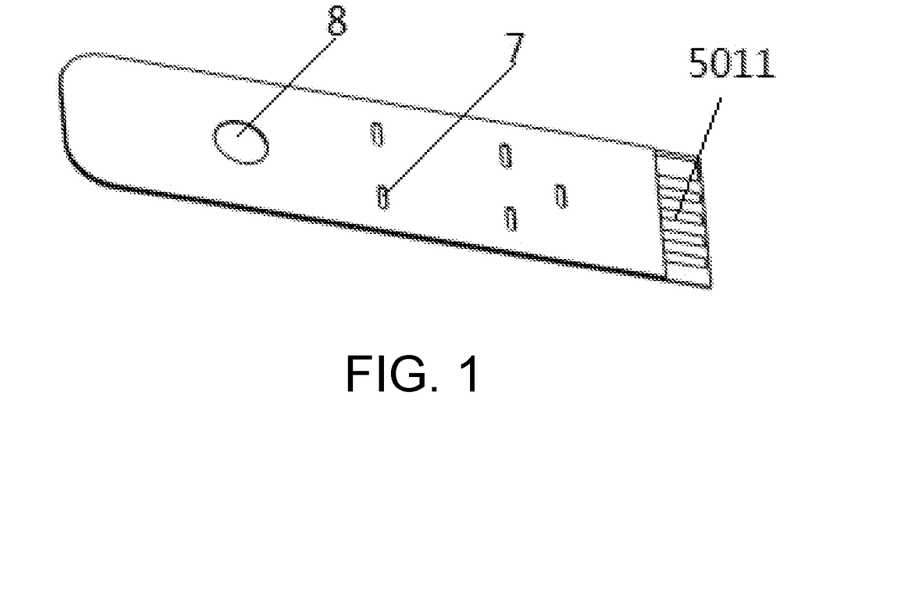
FIG. 1 is a schematic three-dimensional structural diagram of a multi-channel microfluidic blood coagulation detection chip according to the present disclosure.
Figure 2:
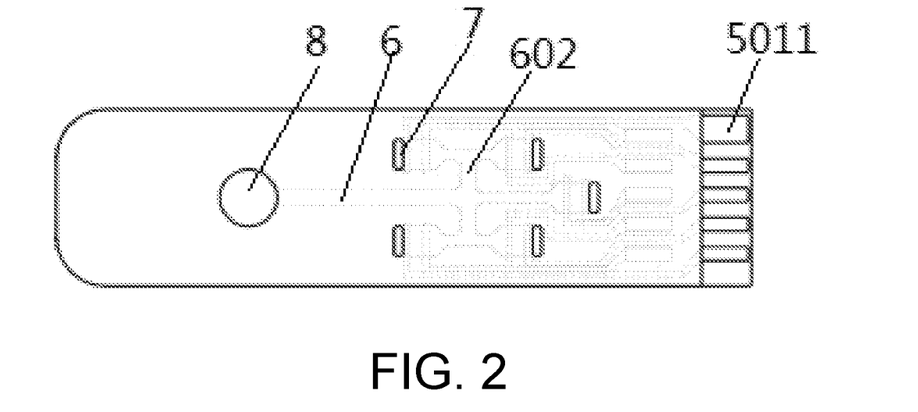
FIG. 2 is a schematic perspective structural diagram of the multi-channel microfluidic blood coagulation detection chip according to the present disclosure.
Figure 3:
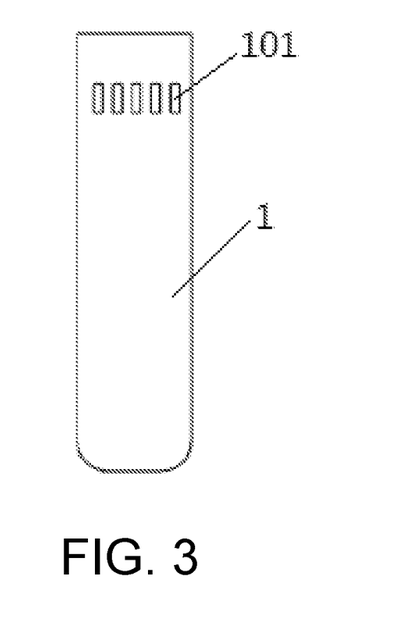
FIG. 3 is an overall rear view of the multi-channel microfluidic blood coagulation detection chip according to the present disclosure.
Figure 4:
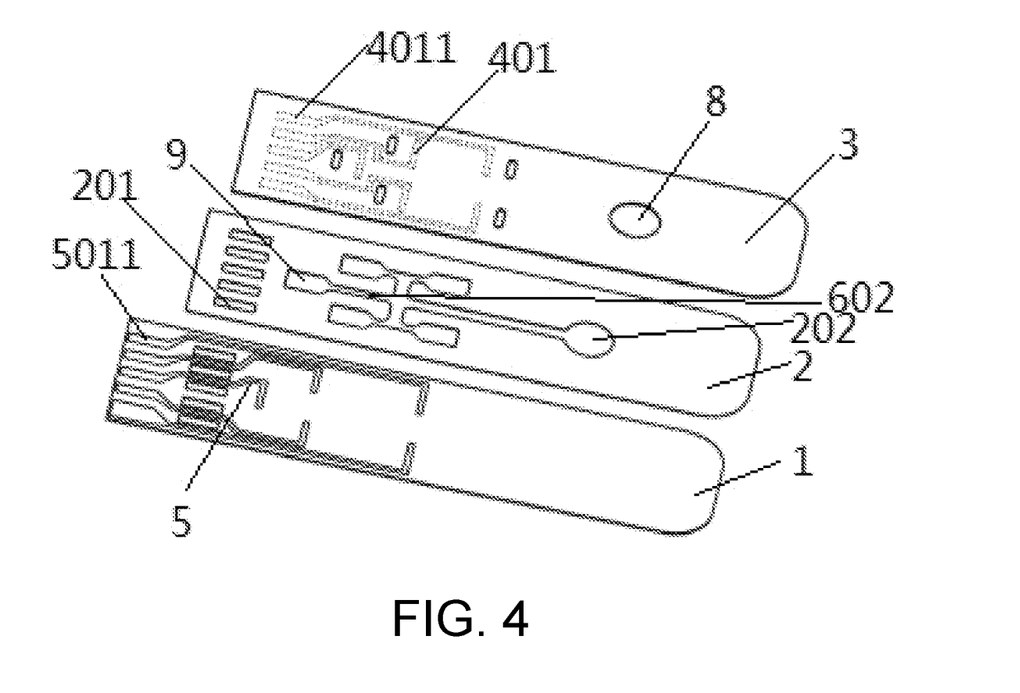
FIG. 4 is a schematic exploded structural diagram of three layers of the multi-channel microfluidic blood coagulation detection chip according to the present disclosure.
Figure 5:
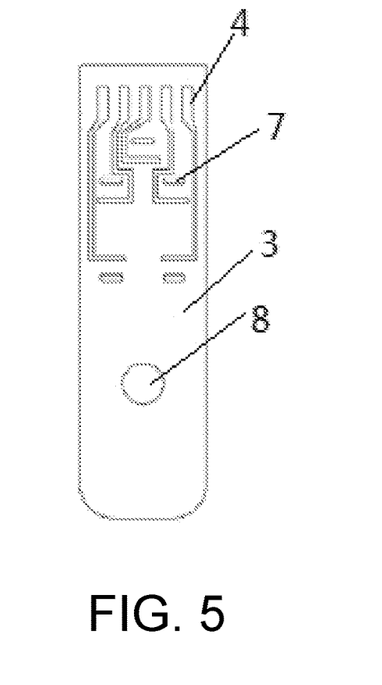
FIG. 5 is a schematic structural diagram of the back surface of an upper-layer chip of the multi-channel microfluidic blood coagulation detection chip according to the present disclosure.
Figure 6:
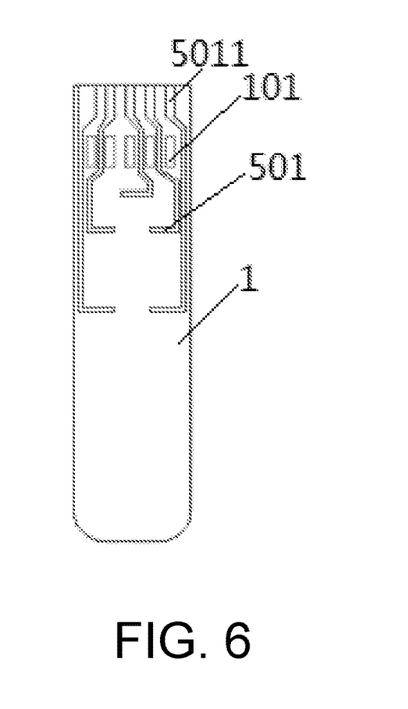
FIG. 6 is a schematic structural diagram of the front surface of a lower-layer chip of the multi-channel microfluidic blood coagulation detection chip according to the present disclosure.
Figure 7:
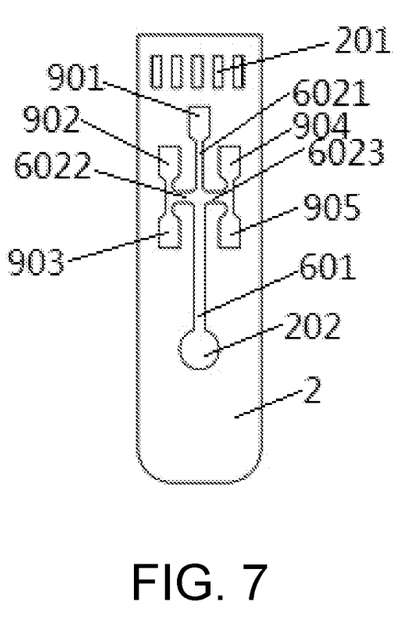
FIG. 7 is a schematic exploded structural diagram of a middle-layer chip of the multi-channel microfluidic blood coagulation detection chip according to the present disclosure.

Embodiment 1. As shown in FIG. 1 to FIG. 7, the multi-channel microfluidic blood coagulation detection chip includes a chip body. The chip body includes, in sequence from bottom to top, a lower-layer chip 1, a middle-layer chip 2, and an upper-layer chip 3. The lower-layer chip 1, the middle-layer chip 2, and the upper-layer chip 3 cooperate with each other to define a closed microfluidic channel and five mutually-independent detection chambers 9. The upper-layer chip 3 is provided with a sample loading hole 8, and the sample loading hole 8 communicates with the detection chambers 9 through the microfluidic channel 6. The chip body further includes electrodes. The electrodes include upper-layer electrodes 4 and lower-layer electrodes 5, the upper-layer electrodes 4 are disposed on the back surface of the upper-layer chip 3, the lower-layer electrodes 5 are disposed on the front surface of the lower-layer chip 1, and a gap is provided between the upper-layer electrodes 4 and the lower-layer electrodes 5.

Both the upper-layer electrodes 4 on the back surface of the upper-layer chip 3 and the lower-layer electrodes 5 on the front surface of the lower-layer chip 1 are arranged corresponding to positions where the detection chambers 9 of the middle-layer chip 2 are located, and the upper-layer electrodes 4 and the lower-layer electrodes 5 communicate with each other through the detection chambers 9. Detection reagents are pre-embedded in the detection chambers 9, after blood to be tested flows into the detection chambers 9, both the upper-layer electrodes 4 and the lower-layer electrodes 5 are in contact with the blood in the detection chambers 9, thereby realizing electrically conductive communication through the blood.

The middle-layer chip 2 is provided with middle-layer communication holes 201 at positions corresponding to the upper-layer electrodes 4, the lower-layer chip 1 is provided with lower-layer communication holes 101 at positions corresponding to the upper-layer electrodes 4, and the upper-layer electrodes 4 are in contact and connection with a detection instrument through the middle-layer communication holes 201 and the lower-layer communication holes 101. Such a setting enables the upper-layer electrodes 4 on the back surface of the upper-layer chip 3 to be in direct contact and connection with the detection instrument.

Both the microfluidic channel 6 and the detection chambers 9 run through the middle-layer chip 2. The microfluidic channel 6 includes a main flow channel 601 and five branching microfluidic channels 602, the tail end of the main flow channel 601 is divided into the five branching microfluidic channels 602, and the five branching microfluidic channels 602 communicate in one-to-one correspondence with the five independent detection chambers 9. The front end of the main flow channel 601 communicates with the sample loading hole 8.

The upper-layer electrodes 4 include five first electrodes 401, and the five first electrodes 401 are all arranged in one-to-one correspondence with the five mutually-independent detection chambers 9. The lower-layer electrodes 5 include five second electrodes 501, the five second electrodes 501 are all arranged in one-to-one correspondence with the five mutually-independent detection chambers 9, and the first electrodes 401 and the second electrodes 501 are respectively working electrodes or reference electrodes.

The first electrode 401 and the second electrode 501 are correspondingly provided for each detection chamber 9, respectively, so as to separate the electrodes of each detection chamber 9, thereby reducing the interference between the electrodes, and improving the detection accuracy. One ends of the five first electrodes 401 are arranged in one-to-one correspondence with the five mutually-independent detection chambers 9 and located in the detection chambers 9, and the other ends of the five first electrodes 401 extend on the back surface of the upper-layer chip 3 to the end head of one end of the upper-layer chip 3 to form connection ends 4011 in contact and connection with the detection instrument. Such a setting enables the first electrode 401 corresponding to each detection chamber to be in direct contact and connection with the detection instrument through the connection end 4011, thereby reducing interference with the second electrode 501.

One ends of the five second electrodes 501 are arranged in one-to-one correspondence with the five mutually-independent detection chambers 9 and located in the detection chambers 9, and the other ends of the plurality of second electrodes 501 extend on the front surface of the lower-layer chip 1 to the end head of one end of the lower-layer chip 1 to form detection ends 5011 in connection with the detection instrument, and the detection ends 5011 are exposed outside the end of an integral whole, formed by bonding the lower-layer chip 1, the middle-layer chip 2 and the upper-layer chip 3, with respect to the upper-layer chip 3 and the middle-layer chip 2. Such a setting enables the detection ends 5011 of the lower-layer chip 1 to be directly inserted into the detection instrument, thereby avoiding interference with the upper-layer electrodes 4.

The upper-layer chip 3 is further provided with five vent holes 7, and the five vent holes 7 are all arranged in one end of the upper-layer chip 3 and disposed at positions corresponding to the detection chambers 9. By providing the five vent holes 7 that run through the upper-layer chip 3, the flow resistance of the fluid to be tested is reduced, so that the flow is faster, and the detection chambers 9 can be quickly filled. The setting of the vent holes 7 facilitates the flow of the sample and is convenient for sample injection. If there is no vent hole 7, the sample cannot flow into the detection chambers 9 for reaction, and the detection reagents are pre-embedded in the detection chambers 9.

The connection ends 4011 are arranged in one-to-one correspondence with the middle-layer communication holes 201 and the lower-layer communication holes 101, respectively. One middle-layer communication hole 201 corresponds to one lower-layer communication hole 101 and to one connection end 4011. In this way, each first electrode 401 can be in contact with the detection instrument.

The middle-layer chip 2 is provided with a liquid receiving port 202, the liquid receiving port 202 is disposed corresponding to the position of the sample loading hole 8, and one end of the main flow channel 601 is connected to the liquid receiving port 202, i.e., one end of the main flow channel 601 communicates with the sample loading hole 8 through the liquid receiving port 202. The other end of the main flow channel 6 is connected to the detection chambers 9 through the branching microfluidic channels 602, and the width of the detection chambers 9 is greater than the width of the branching microfluidic channels 602.

The main flow channel 601 extends in a horizontal direction to the end away from the liquid receiving port 202 to be provided with a first branching microfluidic channel 6021 that is connected to a first detection chamber 901. The main flow channel 601 extends in a vertical direction to the end away from the liquid receiving port 202 towards both sides respectively to be provided with a second branching microfluidic channel 6022 and a third branching microfluidic channel 6023. The second branching microfluidic channel 6022 extends in a direction parallel to the main flow channel 601 to both ends respectively to connect to a second detection chamber 902 and a third detection chamber 903, and the third branching microfluidic channel 6023 extends in the direction parallel to the main flow channel 601 to both ends respectively to connect to a fourth detection chamber 904 and a fifth detection chamber 905. Designing the plurality of channels and the plurality of detection chambers in a specific structural form to guide the flow of the blood sample allows for simultaneous injection of the sample from one sample chamber into five reaction chambers, which makes the flow faster and improves the detection efficiency. In addition, such a design decreases the size of the multi-channel microfluidic blood coagulation detection chip. Compared with the multi-channel microfluidic blood coagulation detection chip of a three-layer structure previously claimed by the applicant, the length and width are decreased by 25~45%, therefore, the production cost is lowered, and the chip is smaller and more portable.

The number of both the first electrodes 401 and the second electrodes 501 is five, and correspondingly, the number of both the middle-layer communication holes 201 and the lower-layer communication holes 101 is five.

Each of the connection ends 4011 is a rectangle of the same size, and the spacing between each two of the connection ends 4011 is equal. Correspondingly, each of the middle-layer communication holes 201 and each of the lower-layer communication holes 101 are both rectangles of the same size, and the spacing between each two of the middle-layer communication holes 201 and the spacing between each two of the lower-layer communication holes 101 are both equal. The size of the connection ends 4011 is greater than or equal to the size of the middle-layer communication holes 201 and the lower-layer communication holes 101. The middle-layer communication holes 201 have the same size as the lower-layer communication holes 101.

The shape of each of the detection ends 5011 is rectangular and the spacing between each two of the detection ends 5011 is equal. The length of the detection ends 5011 exposed outside the end of the integral whole that is formed by bonding the lower-layer chip 1, the middle-layer chip 2 and the upper-layer chip 3, with respect to the upper-layer chip 3 and the middle-layer chip 2 is not more than 1 cm.

The five vent holes 7 are all disposed in the end portions of the detection chambers 9 away from the branching microfluidic channels 602 and at corresponding positions flush with the edges of the detection chambers 9.

Embodiment 2. The multi-channel microfluidic blood coagulation detection chip includes a chip body. The chip body includes, in sequence from bottom to top, a lower-layer chip 1, a middle-layer chip 2, and an upper-layer chip 3. The lower-layer chip 1, the middle-layer chip 2, and the upper-layer chip 3 cooperate with each other to define a closed microfluidic channel and five mutually-independent detection chambers 9. The upper-layer chip 3 is provided with a sample loading hole 8, and the sample loading hole 8 communicates with the detection chambers 9 through the microfluidic channel 6. The chip body further includes electrodes. The electrodes include upper-layer electrodes 4 and lower-layer electrodes 5, the upper-layer electrodes 4 are disposed on the back surface of the upper-layer chip 3, the lower-layer electrodes 5 are disposed on the front surface of the lower-layer chip 1, and a gap is provided between the upper-layer electrodes 4 and the lower-layer electrodes 5.

Both the upper-layer electrodes 4 on the back surface of the upper-layer chip 3 and the lower-layer electrodes 5 on the front surface of the lower-layer chip 1 are arranged corresponding to positions where the detection chambers 9 of the middle-layer chip 2 are located, and the upper-layer electrodes 4 and the lower-layer electrodes 5 communicate with each other through the detection chambers 9. Detection reagents are pre-embedded in the detection chambers 9, after blood to be tested flows into the detection chambers 9, both the upper-layer electrodes 4 and the lower-layer electrodes 5 are in contact with the blood in the detection chambers 9, thereby realizing electrically conductive communication through the blood.

The middle-layer chip 2 is provided with middle-layer communication holes 201 at positions corresponding to the upper-layer electrodes 4, the lower-layer chip 1 is provided with lower-layer communication holes 101 at positions corresponding to the upper-layer electrodes 4, and the upper-layer electrodes 4 are in contact and connection with a detection instrument through the middle-layer communication holes 201 and the lower-layer communication holes 101. Such a setting enables the upper-layer electrodes 4 on the back surface of the upper-layer chip 3 to be in direct contact and connection with the detection instrument.

Both the microfluidic channel 6 and the detection chambers 9 run through the middle-layer chip 2. The microfluidic channel 6 includes a main flow channel 601 and five branching microfluidic channels 602, the tail end of the main flow channel 601 is divided into the five branching microfluidic channels 602, and the five branching microfluidic channels 602 communicate in one-to-one correspondence with the five independent detection chambers 9. The front end of the main flow channel 601 communicates with the sample loading hole 8.

The upper-layer electrodes 4 include five first electrodes 401, and the five first electrodes 401 are all arranged in one-to-one correspondence with the five mutually-independent detection chambers 9. The lower-layer electrodes 5 include five second electrodes 501, the five second electrodes 501 are all arranged in one-to-one correspondence with the five mutually-independent detection chambers 9, and the first electrodes 401 and the second electrodes 501 are respectively working electrodes or reference electrodes. The first electrode 401 and the second electrode 501 are correspondingly provided for each detection chamber 9, respectively, so as to separate the electrodes of each detection chamber 9, thereby reducing the interference between the electrodes, and improving the detection accuracy.

One ends of the five first electrodes 401 are arranged in one-to-one correspondence with the five mutually-independent detection chambers 9 and located in the detection chambers 9, and the other ends of the five first electrodes 401 extend on the back surface of the upper-layer chip 3 to the end head of one end of the upper-layer chip 3 to form connection ends 4011 in contact and connection with the detection instrument. Such a setting enables the first electrode 401 corresponding to each detection chamber to be in direct contact and connection with the detection instrument through the connection end 4011, thereby reducing interference with the second electrode 501.

One ends of the five second electrodes 501 are arranged in one-to-one correspondence with the five mutually-independent detection chambers 9 and located in the detection chambers 9, and the other ends of the plurality of second electrodes 501 extend on the front surface of the lower-layer chip 1 to the end head of one end of the lower-layer chip 1 to form detection ends 5011 in connection with the detection instrument, and the detection ends 5011 are exposed outside the end of an integral whole, formed by bonding the lower-layer chip 1, the middle-layer chip 2 and the upper-layer chip 3, with respect to the upper-layer chip 3 and the middle-layer chip 2. Such a setting enables the detection ends 5011 of the lower-layer chip 1 to be directly inserted into the detection instrument, thereby avoiding interference with the upper-layer electrodes 4.

The upper-layer chip 3 is further provided with five vent holes 7, and the five vent holes 7 are all arranged in one end of the upper-layer chip 3 and disposed at positions corresponding to the detection chambers 9. By providing the five vent holes 7 that run through the upper-layer chip 3, the flow resistance of the fluid to be tested is reduced, so that the flow is faster, and the detection chambers 9 can be quickly filled. The setting of the vent holes 7 facilitates the flow of the sample and is convenient for sample injection. If there is no vent hole 7, the sample cannot flow into the detection chambers 9 for reaction, and the detection reagents are pre-embedded in the detection chambers 9.

The connection ends 4011 are arranged in one-to-one correspondence with the middle-layer communication holes 201 and the lower-layer communication holes 101, respectively. One middle-layer communication hole 201 corresponds to one lower-layer communication hole 101 and to one connection end 4011. In this way, each first electrode 401 can be in contact with the detection instrument.

The middle-layer chip 2 is provided with a liquid receiving port 202, the liquid receiving port 202 is disposed corresponding to the position of the sample loading hole 8, and one end of the main flow channel 601 is connected to the liquid receiving port 202, i.e., one end of the main flow channel 601 communicates with the sample loading hole 8 through the liquid receiving port 202. The other end of the main flow channel 6 is connected to the detection chambers 9 through the branching microfluidic channels 602, and the width of the detection chambers 9 is greater than the width of the branching microfluidic channels 602.

The main flow channel 601 extends in a horizontal direction to the end away from the liquid receiving port 202 to be provided with a first branching microfluidic channel 6021 that is connected to a first detection chamber 901. The main flow channel 601 extends in a vertical direction to the end away from the liquid receiving port 202 towards both sides respectively to be provided with a second branching microfluidic channel 6022 and a third branching microfluidic channel 6023. The second branching microfluidic channel 6022 extends in a direction parallel to the main flow channel 601 to both ends respectively to connect to a second detection chamber 902 and a third detection chamber 903, and the third branching microfluidic channel 6023 extends in the direction parallel to the main flow channel 601 to both ends respectively to connect to a fourth detection chamber 904 and a fifth detection chamber 905. Designing the main flow channel 601 and the five branching microfluidic channels 602 in a specific structural form to guide the flow of the blood sample allows for simultaneous injection of the sample from one sample chamber into five reaction chambers, which makes the flow faster and improves the detection efficiency. In addition, such a design decreases the size of the multi-channel microfluidic blood coagulation detection chip. Compared with the multi-channel microfluidic blood coagulation detection chip of a three-layer structure previously claimed by the applicant, the length and width are decreased by 25%~45%, therefore, the production cost is lowered, and the chip is smaller and more portable.

The number of both the first electrodes 401 and the second electrodes 501 is five, and correspondingly, the number of both the middle-layer communication holes 201 and the lower-layer communication holes 101 is five.

Each of the connection ends 4011 is a rectangle of the same size, and the spacing between each two of the connection ends 4011 is equal. Correspondingly, each of the middle-layer communication holes 201 and each of the lower-layer communication holes 101 are both rectangles of the same size, and the spacing between each two of the middle-layer communication holes 201 and the spacing between each two of the lower-layer communication holes 101 are both equal. The size of the connection ends 4011 is greater than or equal to the size of the middle-layer communication holes 201 and the lower-layer communication holes 101. The middle-layer communication holes 201 have the same size as the lower-layer communication holes 101.

The shape of each of the detection ends 5011 is rectangular and the spacing between each two of the detection ends 5011 is equal. The length of the detection ends 5011 exposed outside the end of the integral whole that is formed by bonding the lower-layer chip 1, the middle-layer chip 2 and the upper-layer chip 3, with respect to the upper-layer chip 3 and the middle-layer chip 2 is not more than 1 cm.

The five vent holes 7 are all disposed in the end portions of the detection chambers 9 away from the branching microfluidic channels 602 and at corresponding positions flush with the edges of the detection chambers 9.

The lower-layer chip 1, the middle-layer chip 2, and the upper-layer chip 3 are bonded into an integral whole by double-sided gluing of the middle-layer chip 2. The middle-layer chip 2 is a pressure-sensitive adhesive tape, the material for the upper-layer chip 3 and/or the lower-layer chip 1 is any one of PMMA, PP, PE, and PET, and the surfaces of the upper-layer chip 3 and the lower-layer chip 1 each are provided with a hydrophilic membrane, so that the sample quickly flows into the main flow channel 601 through the sample loading hole 8, and then separately flows to each branching microfluidic channel 602.

The thickness of the middle-layer chip 2 is 0.1~1.0 mm. The surface of the lower-layer chip 1 is level, the depth of the closed microfluidic channel defined by the lower-layer chip 1, the middle-layer chip 2, and the upper-layer chip 3 in cooperation is 0.1~1.0 mm, and the widths of the detection chambers 9 defined by the three layers of chips in cooperation are 1.0~2.0 mm.

Each of the branching microfluidic channels 602 is provided with a nozzle at a junction with the detection chamber 9. The thickness of the electrodes is 0.5 mm. Nozzles are provided at the junctions between the branching microfluidic channels 602 and the detection chambers 9 to enable the sample to flow into the detection chamber 9 more easily and quickly. The function of the electrodes is to receive signals generated by blood reaction in the detection chambers while applying an alternating-current voltage.

The detection ends 5011 and the connection ends 4011 are inserted into the detection instrument to monitor electrochemical signals generated by reaction, and work in conjunction with the supporting detection instrument to obtain detection results. The detection ends 5011 of the lower-layer electrodes 5 are the portions of the integral whole, formed by bonding the lower-layer chip 1, the middle-layer chip 2 and the upper-layer chip 3, that are exposed with respect to the upper-layer chip 3 and the middle-layer chip 2, so that the detection ends 5011 can be inserted into the detection instrument more easily and conveniently.

During Specific Use:

A blood sample is injected into the sample loading hole 8. The sample simultaneously flows from the liquid receiving port 202 to the five branching microfluidic channels 602 through the main flow channel 601, and then enters the five mutually-independent detection chambers 9. The sample reacts with the detection reagents pre-embedded in the detection chambers 9. In addition, the upper-layer electrodes 4 communicate with the lower-layer electrodes 5 through the detection chambers 9. The multi-channel microfluidic blood coagulation detection chip is inserted into the supporting detection instrument through the connection ends 4011 and the detection ends 5011. By means of an alternating-current resistance method, detection results are obtained by monitoring electrochemical signals generated by the reaction. In this way, five coagulation indexes can be detected simultaneously, a multi-channel effect is achieved, and the detection efficiency is improved. Furthermore, by arranging the upper-layer electrodes 4 and the lower-layer electrodes 5 in different layers, the interference between the electrodes is reduced, and the detection accuracy is improved.

The basic principles, major features and advantages of the present disclosure are shown and described above. A person skilled in the art should understand that the present disclosure is not limited by the foregoing embodiments. The foregoing embodiments and the description are descriptive to only illustrate the principles of the present disclosure. Various changes and improvements, such as some other slight adjustments of the shape and structure of the sample loading hole, or some adjustments of the shape and number of the detection chambers, can also made to the present disclosure, without departing from the spirit and the scope of the present disclosure. These changes and improvements all fall within the scope of protection of the present disclosure. The scope of protection claimed by the present disclosure is defined by the appended claims and equivalents thereof.

What is claimed is:

1. A multi-channel microfluidic blood coagulation detection chip, comprising a chip body, wherein the chip body comprises a lower-layer chip, a middle-layer chip, and an upper-layer chip arranged in sequence from bottom to top; the lower-layer chip, the middle-layer chip, and the upper-layer chip cooperate with each other to define a closed microfluidic channel and a plurality of mutually-independent detection chambers, the upper-layer chip is provided with a sample loading hole, and the sample loading hole communicates with the detection chambers through the microfluidic channel; the chip body further comprises electrodes, the electrodes comprise upper-layer electrodes and lower-layer electrodes, the upper-layer electrodes are disposed on a back surface of the upper-layer chip, the lower-layer electrodes are disposed on a front surface of the lower-layer chip, and a gap is provided between the upper-layer electrodes and the lower-layer electrodes, wherein both the upper-layer electrodes on the back surface of the upper-layer chip and the lower-layer electrodes on the front surface of the lower-layer chip are arranged corresponding to positions where the detection chambers of the middle-layer chip are located, and the upper-layer electrodes and the lower-layer electrodes communicate with each other through the detection chambers; and wherein the middle-layer chip is provided with middle-layer communication holes at positions corresponding to the upper-layer electrodes, the lower-layer chip is provided with lower-layer communication holes at positions corresponding to the upper-layer electrodes, and the upper-layer electrodes are in contact and connection with a detection instrument through the middle-layer communication holes and the lower-layer communication holes.

2. The multi-channel microfluidic blood coagulation detection chip according to claim 1, wherein both the microfluidic channel and the detection chambers run through the middle-layer chip; the microfluidic channel comprises a main flow channel and a plurality of branching microfluidic channels, a tail end of the main flow channel is divided into the plurality of branching microfluidic channels, and the plurality of branching microfluidic channels communicate in one-to-one correspondence with the plurality of mutually-independent detection chambers; and a front end of the main flow channel communicates with the sample loading hole.

3. The multi-channel microfluidic blood coagulation detection chip according to claim 2, wherein the upper-layer electrodes comprise a plurality of first electrodes, and the plurality of first electrodes are all arranged in one-to-one correspondence with the plurality of mutually-independent detection chambers; the lower-layer electrodes comprise a plurality of second electrodes, the plurality of second electrodes are all arranged in one-to-one correspondence with the plurality of mutually-independent detection chambers, and the first electrodes and the second electrodes are respectively working electrodes or reference electrodes.

4. The multi-channel microfluidic blood coagulation detection chip according to claim 3, wherein one ends of the plurality of first electrodes are arranged in one-to-one correspondence with the plurality of mutually-independent detection chambers and located in the detection chambers, and the other ends of the plurality of first electrodes extend on the back surface of the upper-layer chip to an end head of one end of the upper-layer chip to form connection ends in contact and connection with the detection instrument.

5. The multi-channel microfluidic blood coagulation detection chip according to claim 3, wherein one ends of the plurality of second electrodes are arranged in one-to-one correspondence with the plurality of mutually-independent detection chambers and located in the detection chambers, and the other ends of the plurality of second electrodes extend on the front surface of the lower-layer chip to an end head of one end of the lower-layer chip to form detection ends in connection with the detection instrument, and the detection ends are exposed outside an end of an integral whole that is formed by bonding the lower-layer chip, the middle-layer chip and the upper-layer chip, with respect to the upper-layer chip and the middle-layer chip.

6. The multi-channel microfluidic blood coagulation detection chip according to claim 2, wherein the upper-layer chip is further provided with a plurality of vent holes, and the plurality of vent holes are all arranged in one end of the upper-layer chip and disposed at positions corresponding to the detection chambers.

7. The multi-channel microfluidic blood coagulation detection chip according to claim 4, wherein the connection ends are arranged in one-to-one correspondence with the middle-layer communication holes and the lower-layer communication holes, respectively.

8. The multi-channel microfluidic blood coagulation detection chip according to claim 2, wherein the middle-layer chip is provided with a liquid receiving port, the liquid receiving port is disposed corresponding to a position of the sample loading hole, one end of the main flow channel is connected to the liquid receiving port, the other end of the main flow channel is connected to the detection chambers through the branching microfluidic channels, and a width of the detection chambers is greater than a width of the branching microfluidic channels.

9. The multi-channel microfluidic blood coagulation detection chip according to claim 8, wherein the main flow channel extends in a horizontal direction to an end away from the liquid receiving port to be provided with a first branching microfluidic channel that is connected to a first detection chamber; the main flow channel extends in a vertical direction to the end away from the liquid receiving port towards both sides respectively to be provided with a second branching microfluidic channel and a third branching microfluidic channel; the second branching microfluidic channel extends in a direction parallel to the main flow channel to both ends respectively to connect to a second detection chamber and a third detection chamber, and the third branching microfluidic channel extends in the direction parallel to the main flow channel to both ends respectively to connect to a fourth detection chamber and a fifth detection chamber.

10. The multi-channel microfluidic blood coagulation detection chip according to claim 7, wherein a number of both the first electrodes and the second electrodes is five, and correspondingly, a number of both the middle-layer communication holes and the lower-layer communication holes is five.

11. The multi-channel microfluidic blood coagulation detection chip according to claim 7, wherein each of the connection ends is a rectangle having same size, and a spacing between each two of the connection ends is equal; correspondingly, each of the middle-layer communication holes and each of the lower-layer communication holes are both rectangles having same size, and a spacing between each two of the middle-layer communication holes and a spacing between each two of the lower-layer communication holes are both equal; a size of the connection ends is greater than or equal to a size of the middle-layer communication holes and the lower-layer communication holes; and the middle-layer communication holes have the same size as the lower-layer communication holes.

12. The multi-channel microfluidic blood coagulation detection chip according to claim 5, wherein a shape of each of the detection ends is rectangular and a spacing between each two of the detection ends is equal; and a length of the detection ends exposed outside the end of the integral whole that is formed by bonding the lower-layer chip, the middle-layer chip and the upper-layer chip, with respect to the upper-layer chip and the middle-layer chip is not more than 1 cm.

13. The multi-channel microfluidic blood coagulation detection chip according to claim 6, wherein the plurality of the vent holes are all disposed in end portions of the detection chambers away from the branching microfluidic channels and at corresponding positions flush with edges of the detection chambers.

\* \* \* \* \*